United States Patent
Xu et al.

(10) Patent No.: US 12,283,354 B2
(45) Date of Patent: Apr. 22, 2025

(54) METHOD FOR ESTIMATING EFFECTIVE PRESTRESS AND CALCULATING EVALUATION CHARACTERISTIC VALUE OF CONCRETE STRUCTURE

(71) Applicant: CENTRAL RESEARCH INSTITUTE OF BUILDING AND CONSTRUCTION CO., LTD. MCC, Beijing (CN)

(72) Inventors: Qing Xu, Beijing (CN); Bin Zeng, Beijing (CN); Xiaoda Xu, Beijing (CN); Jiawei Li, Beijing (CN); Haoda Zhang, Beijing (CN); Yanyan Wang, Beijing (CN)

(73) Assignee: CENTRAL RESEARCH INSTITUTE OF BUILDING AND CONSTRUCTION CO., LTD. MCC, Beijing (CN)

( * ) Notice: Subject to any disclaimer, the term of this patent is extended or adjusted under 35 U.S.C. 154(b) by 0 days.

(21) Appl. No.: 18/817,274

(22) Filed: Aug. 28, 2024

(65) Prior Publication Data

US 2024/0420809 A1 Dec. 19, 2024

Related U.S. Application Data

(63) Continuation of application No. PCT/CN2024/099717, filed on Jun. 18, 2024.

(30) Foreign Application Priority Data

Oct. 8, 2023 (CN) .......................... 202311289576.X

(51) Int. Cl.
*G16C 60/00* (2019.01)

(52) U.S. Cl.
CPC .................... *G16C 60/00* (2019.02)

(58) Field of Classification Search
CPC ....................................................... G16C 60/00
See application file for complete search history.

(56) References Cited

FOREIGN PATENT DOCUMENTS

| CN | 105427018 A | * | 3/2016 | ......... G06Q 10/0639 |
| CN | 112414649 A | * | 2/2021 | ......... G01M 5/0008 |

(Continued)

OTHER PUBLICATIONS

Eltouny et al., "Unsupervised Learning Methods for Data-Driven Vibration-Based Structural Health Monitoring: A Review", Mar. 20, 2023, Sensor 2023, 23 (6), 3290, pp. 1-40 (Year: 2023).*

(Continued)

*Primary Examiner* — Mi'schita' Henson
(74) *Attorney, Agent, or Firm* — Hemisphere Law, PLLC; Zhigang Ma

(57) ABSTRACT

A concrete structure effective prestress estimation and evaluation characteristic value calculation method which includes calculating effective prestress probability distribution of a concrete structure prestress rebar, establishing a Gaussian mixture model of effective prestress of the concrete structure, carrying out normalization processing and normal significance judgment on the Gaussian mixture model, sampling and estimating the effective prestress probability distribution of the structure with normal distribution in theoretical distribution, calculating effective prestress evaluation characteristic values of the components under the normal distribution condition, grouping processing and normal significance judging of the Gaussian mixture model, sampling and estimating the structural effective prestress probability distribution of the N-sub-distribution Gaussian mixture model by theoretical distribution, calculating effective prestress evaluation characteristic values of the components under the condition of the N-sub-distribution Gaussian mixture model.

8 Claims, 5 Drawing Sheets

(56) References Cited

FOREIGN PATENT DOCUMENTS

| | | | | | |
|---|---|---|---|---|---|
| CN | 114528684 | A | * | 5/2022 | ............. G06F 30/13 |
| CN | 114528706 | A | | 5/2022 | |
| CN | 115510743 | A | * | 12/2022 | |
| CN | 116312873 | A | * | 6/2023 | |
| CN | 117114436 | A | * | 11/2023 | ............. G06F 30/13 |

OTHER PUBLICATIONS

Han et al., Long-Term Prestress Loss Calculation Considering the Interaction of Concrete Shrinkage, Concrete Creep, and Stress Relaxation, 2023, Materials, 16 (6), 2452, pp. 1-14 (Year: 2023).*
Lee et al., A Novelty Detection Approach for Tendons of Prestressed Concrete Bridges Based on a Convolutional Autoencoder and Acceleration Data, 2019, Sensors, 19(7), pp. 1-27 (Year: 2019).*
English translation of CN-112414649-A (Year: 2021).*
English translation of CN-114528684-A (Year: 2022).*
CNIPA, Notification of First Office Action for Chinese application CN202311289576.X, Mar. 28, 2024.
CNIPA, Notification to grant patent right for Chinese application CN202311289576.X, Apr. 12, 2024.

* cited by examiner

METHOD FOR ESTIMATING EFFECTIVE PRESTRESS AND CALCULATING EVALUATION CHARACTERISTIC VALUE OF CONCRETE STRUCTURE

TECHNICAL FIELD

The disclosure relates to the technical field of prestress concrete structures, and more specifically, to a targeted method for estimating pertinence of effective prestress measured evaluation characteristic values of an existing concrete structure based on sequential sampling theory.

BACKGROUND ART

The prestress technology is a core technology for the construction of important civil engineering and has been widely applied in infrastructure such as public-railway bridges, special structures, house buildings and the like thanks to its low carbon, material saving and strong space spanning capability. In recent years, with the continuous advancement of urban updating, service performance evaluation demands are increasing. The prestress concrete structure is influenced by multiple factors such as fatigue, overload, over-service life and the like, and if the effective prestress is continuously attenuated, the service performance of the structure is gradually reduced, and safety accidents can be caused in serious situations. Therefore, scientific evaluation of the service performance of prestress concrete structures is an important foundation for ensuring their long-term safe service.

The effective prestress level is an important factor affecting the service performance of the prestress concrete structure. In the actual service life, the effective prestress has multisource uncertain influence factors, and has certain randomnesses. The structural prestress system is affected by design factors such as line shape, reinforcement ratio and the like, and has obvious non-uniformity. In addition, prestress rebars have strong concealment and are difficult to be measured. Efficient and accurate detection technology has only been gradually applied in recent years, which is limited by the structure type and the detection efficiency, so that only a small amount of prestress data of scattered effective prestress rebar can be obtained. Therefore, the prestress rebars of the prestressed system of the concrete structure have large quantity, strong uncertainty, uneven distribution and prominent discrete effect. However, the existing evaluation method often uses the average value of the detected data as the evaluation characteristic value of the effective prestress, which ignores the uncertainty and the non-uniformity of the effective prestress distribution, and cannot accurately characterize the prestress performance of the structure, and the evaluation method for the behavior and structural service performance of effective prestressed systems based on measured data is seriously lacking.

Therefore, there is an urgent need by the technicians in the field to provide an estimation method of the real-time probability distribution of the effective prestress of the existing concrete structure based on the actually measured sampling data of the effective prestress, and further scientifically determine the evaluation characteristic value of the effective prestress.

SUMMARY

In view of the above, the present disclosure provides an effective method for evaluating prestress of a concrete structure and calculating an evaluation characteristic value, which aims to solve the above technical problems.

In order to achieve the above purpose, the present disclosure adopts the following technical scheme.

A method for estimating the effective prestress and calculating the evaluation characteristic value of the concrete structure specifically includes the following steps as follows.

In the S1, effective prestress probability distribution of a concrete structure prestress rebar is calculated.

The number n of the prestress rebars in the prestress concrete structure is counted according to the design construction drawing. Based on the statistical characteristics of all influence factors, calculating effective prestress probability distribution (i=1, 2, . . . n) of the ith rebar in the prestress concrete structure by adopting a Monte Carlo method. The statistical parameters of the influence factors such as tension control stress, friction coefficient and the like and the theoretical calculation formula of the prestress loss can refer to paper entitled "the prestress distribution characteristics and the estimation method of the concrete structure based on the Gaussian mixture model, Building Structure report, 2022, 43 (10): 60-67". The probability distribution (i=1, 2, . . . n) of the effective prestress of the ith prestress rebar is calculated by adopting a Monte Carlo method, and establishing a normal distribution probability density curve, wherein the normal distribution probability density curve is shown in a formula (1).

$$p_i(x) = p_i(x \mid \mu_i, s_i^2) \qquad (1)$$
$$= \frac{1}{\sqrt{2\pi} s_i} \exp\left(-\frac{(x-\mu_i)^2}{2s_i^2}\right)$$

Wherein x is the effective prestress, the $\mu_i$ is the design value of effective prestress of the ith rebar and is also the mean value of probability distribution, $s_i$ is the standard deviation.

In the S2, a Gaussian mixture model of effective prestress of the concrete structure is established.

The aggregate of the effective prestress probability distribution of all the prestress rebars (n rebars) in the structural prestress system is regarded as a whole and is defined as the effective prestress of the structureForce probability distribution. The probability density $p_i(x)$ of the effective prestress of the ith (i=1, 2, . . . , n) individual rebar of the structure is obtained through the step S1 and probability density superposition on the composite material is performed to form a Gaussian mixture model with effective prestress, wherein the Gaussian mixture model is shown in a formula (2).

$$P(x) = \sum_{i=1}^{n} \frac{1}{n} \cdot p_i(x \mid \mu_i, s_i^2) \qquad (2)$$
$$= \sum_{i=1}^{n} \frac{1}{n} \cdot \frac{1}{\sqrt{2\pi} s_i} \exp\left(-\frac{(x-\mu_i)^2}{2s_i^2}\right)$$

In the S3, normalization processing and normal significance judgment of the Gaussian mixture model are performed.

Studies have shown that the Gaussian mixture model formed by the sub-distributions with similar mean and variance can be approximately characterized by normal distribution. To reduce the structural effective prestress distribution non-uniformity caused by design factors, normalization can be performed on each single-rib effective prestress, and the random variable of all the single-rib effective prestress is divided by the corresponding design value $\mu_i$. A normalized structure effective prestress Gaussian mixture model is formed as shown in the formula (3).

$$P(x) = \sum_{i=1}^{n} \frac{1}{n} \cdot \frac{1}{\sqrt{2\pi}(s_i/\mu_i)} \exp\left(-\frac{(x-1)^2}{2(s_i/\mu_i)^2}\right) \quad (3)$$

In statistics, the normal significance of the kurtosis bias calculation model may be employed, which can be referred by the paper entitled "concrete structure prestress distribution characteristics based on Gaussian mixture model and estimation method, Building Structure report, 2022, 43 (10): 60-67". The degree of skewness S=0 of the gaussian mixture model with the same mean value of the sub-distribution, and the kurtosis K can be calculated by using formula (4), $$K = \frac{\sum_{i=1}^{n} \omega_i \cdot 3(s_i/\mu_i)^4}{\left(\sum_{i=1}^{n} \omega_i \cdot (s_i/\mu_i)^2\right)^2} \quad (4)$$

if the K value (kurtosis) falls within the range of [3, 3.5], the distribution is initially considered to be approximately compliant with a normal distribution, but further quantitative determinations are required.

A normal distribution model as shown in a formula (5) is constructed based on the mean $\mu=1$ based on equation (3) and variance $$s^2 = \frac{1}{n}\sum_{i=1}^{n}(s_i/\mu_i)^2.$$

$$N(x) = \frac{1}{\sqrt{2\pi}s}\exp\left(-\frac{(x-1)^2}{2s^2}\right) \quad (5)$$

The difference function $D(x)=P(x)-N(x)$ of the Gaussian mixture model and the normal distribution model is established, and as the monotonicity shows, D (x) is the maximum value at the position of x=1, and only the difference value is judged to be within 5%, as shown in a formula (6), the Gaussian mixture model (shown in a formula 3) can be determined to be approximately represented by the normal distribution (shown in a formula 5).

$$\frac{P(1)-N(1)}{N(1)} \leq 5\% \quad (6)$$

In the S4, sampling and estimating the effective prestress probability distribution of the structure with normal distribution as theoretical distribution.

In the actual evaluation engineering, the influence of factors such as construction errors, material properties and the like is considered, and the effective prestress control parameters of the structure are corrected through actually measured sample distribution so as to accurately reflect the actual distribution characteristics of the effective prestress of the structure.

According to the step S3, after the effective prestress probability distribution of the structure is normalized, the effective prestress probability distribution of the structure can pass through a normal significance test, and the average value and the variance of the effective prestress probability distribution of the structure determine the probability distribution form of the effective prestress according to the total body of an approximate normal distribution. However, since accurate estimation of variance requires a large number of sample supports, the measured cost is high. Therefore, the disclosure introduces a 95% assurance rate characteristic value which simultaneously contains mean and variance information as a constraint characteristic value, and carries out measured sampling estimation on structural effective prestress based on the concept of sequential sampling:

(1) the effective prestress of the structure is treated to overall obey normal, as shown in formula (7). Wherein, the $\mu$ and $s^2$ are unknown. Randomly sampling and detecting the effective prestress of the prestress rebar in the structure to obtain the real-time effective prestress of the prestress rebar, and dividing the real-time effective prestress by the design value of the prestress rebar. The first batch of sampling totally extracts k rebars to form $\tilde{X}_1=(\tilde{x}_1, \tilde{x}_2, \ldots, \tilde{x}_k)$ initial samples.

$$P(x) = p(x|\mu, s^2) \quad (7)$$

(2) The Bootstrap method is adopted to test samples $\tilde{X}_1$ The sampling is carried out k×B times, and B Bootstrap samples (shown in formula 8) capable of reflecting the overall statistical characteristics are formed. Wherein one column of the matrix is one Bootstrap sample, and B is taken for at least 100000 times. Calculating the characteristic value of 95% guarantee rate of each Bootstrap sample $\hat{F}$, a characteristic value probability density function $P(\hat{F})$ is formed, 95% confidence interval Length $l_F$ is calculated.

$$\{\tilde{X}_1\} = (\tilde{x}_1, \tilde{x}_2, \ldots, \tilde{x}_k) = \begin{bmatrix} \tilde{x}_{11} & \tilde{x}_{12} & \ldots & \tilde{x}_{1B} \\ \tilde{x}_{21} & \tilde{x}_{22} & \ldots & \tilde{x}_{2B} \\ \vdots & \vdots & \ddots & \vdots \\ \tilde{x}_{k1} & \tilde{x}_{k2} & \ldots & \tilde{x}_{kB} \end{bmatrix} \quad (8)$$

(3) If the maximum error $\lambda=l_F/\hat{F}_\mu \leq 0.05(0.1)$, the estimation accuracy of the sample $\tilde{X}_1$ is then consider as meeting the predetermined requirement. The average value of 0.05 and 0.1 are preset estimated accuracy requirements, 0.05 is preferable when the accuracy requirement is high, and 0.1 is preferable when the accuracy requirement is not high. If $\lambda=l_F/\hat{F}_\mu > 0.05(0.1)$, the estimation of the constraint characteristic value of the sample $\tilde{X}_1$ is then considered as not meeting the preset requirement, m samples need to be continuously extracted until the total sample number is supplemented to k+m, and forming the actually measured sample $\tilde{X}_2=(\tilde{x}_1, \tilde{x}_2, \ldots, \tilde{x}_{k+m})$.

(4) Repeating the steps (2) to (3) for sample $\tilde{X}_2$, and when the estimation accuracy requirement is not met, adding m samples each time, repeating p−1 times in total until the estimation accuracy requirement is met, namely, the maximum estimation error $\lambda=l_F/\hat{F}_\mu \leq 0.05(0.1)$ and the final sample $\tilde{X}_p=(\tilde{x}_1, \tilde{x}_2, \ldots, \tilde{x}_{k+(p-1)m})$ if formed.

(5) Performing sample expansion processing to $\tilde{X}_p$ by Bootstrap method to form probability density function of mean and variance $P(\hat{\mu}_p)$, $P(\hat{s}_p)$ 95% confidence interval of the two parameters $[\hat{\mu}_{p\_L}, \hat{\mu}_{p\_H}]$, $[\hat{s}_{p\_L}^2, \hat{s}_{p\_H}^2]$ are separately calculated. To ensure the safety of the structure, it is recommended to use the lower limit of the mean value $\hat{\mu}_{p\_L}$ and upper bound of sum variance $\hat{s}_{p\_H}^2$ and substitute the characteristic parameters into the formula (7) to obtain an measured probability estimation model of the effective prestress of the structure, wherein the measured probability estimation model is shown in the formula (9).

$$\hat{P}(x) = p(x \mid \hat{\mu}_{p\_L}, \hat{s}_{p\_H}^2) \tag{9}$$

(6) An inverse normalization treatment on the formula (9) is performed, and multiplying the design value $\mu_i$ of each prestress rebar of the structure and calculating a measured probability estimation model of each single-rib effective prestress, wherein the measured probability estimation model is shown in a formula (10).

$$\hat{p}_i(x) = p(x \mid \mu_i \hat{\mu}_{p\_L}, \mu_i^2 \hat{s}_{p\_H}^2) \tag{10}$$

In the S5, effective prestress evaluation characteristic values of the components under normal distribution conditions are calculated.

When the effective prestress of the actually measured structure is subjected to normal distribution, the effective prestress of the single rebar is also subjected to normal distribution (see FIG. 10), and the effective prestress probability distribution of the component is that a plurality of normal distributions are overlapped. Based on the normal distribution superposition principle, the effective prestress probability distribution of the component with T prestress rebars can be expressed as follows:

$$\Phi_T = p\left(x \mid \sum_{R=1}^{T} \mu_R, \sum_{R=1}^{T} s_R^2\right) \tag{11}$$

wherein $\mu_R$ and $s_R$ are the measured estimated mean and standard deviation of the effective prestress of each single rebar in the structure which are respectively obtained by a formula (10), wherein R is the number (R=1, 2, ..., T) of the prestress rebar in the structure.

To fully consider the discrete features of the effective prestress distribution of the structure, the upper limit/lower limit of the 95% confidence interval is adopted as the feature value for evaluating the effective prestress distribution in the component $\hat{\sigma}_{pe}$ which is shown in formula (12). When the prestress effect is beneficial to the component, the lower limit of the 95% confidence interval is adopted for estimation, and the formula takes a negative sign; when the prestress effect is detrimental to the component, the upper 95% confidence interval limit should be used for the estimation, and the formula is positive.

$$\hat{\sigma}_{pe} = \frac{\sum_{r=1}^{T} \mu_r \pm 1.96 \sqrt{\sum_{r=1}^{T} s_r^2}}{T} \tag{12}$$

In the S6, processing and normal significance judging of the Gaussian mixture model are grouped.

When the normal significance cannot be met, returning to the step S2, arranging the effective prestress mean and variance of all the single rebars in the formula (2) according to the size, and dividing the effective prestress mean and variance into N groups so as to minimize the difference between the mean and variance of each group, wherein the number of the prestress rebars in each group is $n_j$. The gaussian mixture model of the effective prestress of the structure is shown in formula (13).

$$P(x) = \sum_{i=1}^{n} \frac{1}{n} \cdot p(x \mid \mu_i, s_i^2) = \sum_{j=1}^{N} \frac{n_j}{n} \sum_{q=1}^{n_j} \frac{1}{n_j} p(x \mid \mu_{qj}, s_{qj}^2) \tag{13}$$

Wherein j represents a packet number (j=1, 2 ... N), nj is the number of rebars in each group, q represents the rebar number (q=1, 2, ... nj), $\mu_{qj}, s_{qj}^2$ respectively are the design value (mean) and variance of the q-th rebar in the j-th group $$P(x) = \sum_{j=1}^{N} \frac{n_j}{n} \sum_{q=1}^{n_j} \frac{1}{n_j} p(x \mid \mu_{qj}, s_{qj}^2)$$

Referring to the paper entitled "concrete structure prestress distribution characteristics based on Gaussian mixture model and estimation method, Building Structure report, 2022, 43 (10): 60-67", the kurtosis and skewness of each group of Gaussian mixture models are calculated by adopting the following steps:

$$S = \frac{E[(x - \mu_j)^3]}{E[(x - \mu_j)^2]^{3/2}} \tag{14}$$

$$K = \frac{E[(x - \mu_j)^4]}{E[(x - \mu_j)^2]^2} \tag{15}$$

$$E[(x - \mu_j)^2] = \sum_{q=1}^{n_j} \frac{1}{n_j} s_{qj}^2 + \left[\sum_{q=1}^{n_j} \frac{1}{n_j} \mu_{qj}^2 - \mu_j^2\right] \tag{16}$$

$$E[(x - \mu_j)^3] = \tag{17}$$

$$3\left[\sum_{q=1}^{n_j} \frac{1}{n_j} (\mu_{qj} - \mu_j)\right] s_{qj}^2 + \sum_{q=1}^{n_j} \frac{1}{n_j} [\mu_q^3 - 3\mu_j \mu_{qj}^2 + 3\mu_j^2 \mu_{qj}] - 3\mu_j^3$$

$$E[(x - \mu_j)^4] = \sum_{q=1}^{n_j} \frac{1}{n_j} \cdot 3 s_{qj}^4 + \sum_{q=1}^{n_j} \frac{1}{n_j} \cdot (6\mu_{qj}^2 + 6\mu_j^2 - 12\mu_j \mu_{qj}) s_{qj}^2 + \tag{18}$$

$$\sum_{q=1}^{n_j} \frac{1}{n_j} \cdot (\mu_{qj}^4 - 4\mu_j \mu_{qj}^3 + 6\mu_j^2 \mu_{qj}^2 - 4\mu_j^3 \mu_{qj}) + \mu_j^4$$

wherein: S is skewness, K is kurtosis, $E[(x-\mu_j)^2]$, $E[(x-\mu_j)^3]$, $E[(x-\mu_j)^4]$ respectively are the center distances of the second order, the third order and the fourth order of the jth group. The mean of the values $\mu_j$ is designed for the j-th set of models, $$\mu_j = \sum_{q=1}^{n_j} \frac{1}{n_j} \mu_{qj}.$$

If the skewness S of the j-th Gaussian mixture model is in the range of [−0.2,0.2] and the kurtosis K is in the range of [3, 3.5], the model can approximately follow normal distribution.

If the N groups of gaussian mixture models can pass the normal significance test, the structural effective prestress gaussian mixture model can be approximately converted into an N-sub-distribution gaussian mixture model, so that each sub-distribution can be approximately represented by a normal distribution, as shown in a formula (19).

$$P(x) = \sum_{i=1}^{n} \omega_i \cdot p(x \mid \mu_i, s_i^2) \approx \sum_{j=1}^{N} \omega_j p(x \mid \mu_j, s_j^2) \qquad (19)$$

The N is the grouping number. In practical engineering, it is recommended that N be firstly 2, and if the normal significance criterion cannot be satisfied, the number of packets is increased, so that N=N+1, and finally N sub-distributions can pass the normal significance test. For general engineering, 2≤N≤5 is recommended. $\omega_j$ is the weight of the j-th group.

In the S7, the structural effective prestress probability distribution of the N-sub-distribution Gaussian mixture model by theoretical distribution are sampled and estimated.

When the effective prestress probability distribution of the structure can be processed and verified in step S6, it can be considered that the effective prestress probability distribution of the structure is derived from a population of Gaussian mixture distribution of approximately N-sub-distribution, as shown in a formula (20).

$$P(x) = \sum_{j=1}^{N} \omega_j p(x \mid \mu_j, s_j^2) \qquad (20)$$

The actual sample estimation is performed with reference to the normally distributed actual sample estimation (step S5) for the effective prestress of the structure. The method includes the following specific steps.

(1) The effective prestress of the structure is treated to obey the N-sub-distribution Gaussian mixture mode, wherein $\omega_j$, $\mu_j$ and $s_j$ are unknown. The population is sampled for the first time, and k initial samples are extracted $\tilde{X}_1 = (\tilde{x}_1, \tilde{x}_2, \ldots, \tilde{x}_k)$ (2) The Bootstrap method is adopted, and sampling with replacement on sample $\tilde{X}_1$ is performed k×B times to form B Bootstrap samples capable of reflecting overall statistical characteristics.

(3) The statistical parameters such as $\omega_j$, $\mu_j$, and $s_j$ for each Bootstrap sample are estimated by EM algorithm, the probability distribution P($\hat{F}$) of the characteristic value with a 95% guarantee rate is obtained, and 95% confidence interval length $l_F$ is calculated.

(4) If the maximum error is $\lambda = l_F/\hat{F}_\mu \leq 0.05(0.1)$, then it is considered that the estimation accuracy of the sample $\tilde{X}_1$ meets the predetermined requirement; if $\lambda = l_F/\hat{F}_\mu > 0.05(0.1)$, then it is considered that the estimation of the sample $\tilde{X}_1$ on the characteristic value cannot meet the preset requirement, m samples are extracted continuously to supplement the total sample number to k+m and the actually measured sample $\tilde{X}_2 = (\tilde{x}_1, \tilde{x}_2, \ldots, \tilde{x}_{k+m})$ is formed.

(5) $\tilde{X}_2$ is used as a sample and the steps ② to ③ are repeated, when the estimation accuracy requirement is not met, m samples is added each time, which is repeated p−1 times in total until the estimation accuracy requirement, namely, maximum estimation error $\lambda = l_F/\hat{F}_\mu \leq 0.05(0.1)$, is met, and finally sample $\tilde{X}_2 = (\tilde{x}_1, \tilde{x}_2, \ldots, \tilde{x}_{k+(p-1)m})$ is formed.

(6) each control parameter of the sample $\tilde{X}_p$ is estimated by EM algorithm to obtain a weight $\hat{\omega}_j$, mean $\hat{\mu}_j$ and variance $\hat{s}_j$, which are substituted into the formula (20) to obtain the effective prestress probability distribution of the structure;

$$\hat{P}(x) = \sum_{j=1}^{N} \hat{\omega}_j p(x \mid \hat{\mu}_j, \hat{s}_j^2) \qquad (21)$$

In the S8, effective prestress evaluation characteristic values of the components under the condition of the N-sub-distribution Gaussian mixture model is calculated:

When the actually measured distribution of the effective prestress of the structure approximately is subjected to an N-sub-distribution Gaussian mixture model, N=2, 3 and 4, . . . , it can be considered that the effective prestress of a single rebar also obeys the N-sub-distribution Gaussian mixture model. As no relevant report on Gaussian mixture model probability superposition calculation is seen, the Gaussian mixture model superposition formula is deduced based on a normal distribution superposition principle in the present disclosure.

When the effective prestress of the structure is a two-sub-distribution gaussian mixture model, i.e., n=2, as shown in a formula (22).

$$\hat{p}(x) = \hat{\omega}_1 p(x \mid \hat{\mu}_1, \hat{s}_1^2) + \omega_2 p(x \mid \hat{\mu}_2, \hat{s}_2^2) \qquad (22)$$

Based on the probability superposition principle, when two rebars exist in the component, the Gaussian mixture model superposition can be regarded as mutual superposition between two normal sub-distributions with weights. For example, the probability of simultaneous occurrence and mutual superposition of a sub-distribution $p(x|\hat{\mu}_1, \hat{s}_1^2)$ and a sub-distribution $p(x|\hat{\mu}_2, \hat{s}_2^2)$ is $2\omega_1\omega_2$. And because each sub-distribution is normal distribution, the average value and the variance after superposition can be calculated through the normal distribution superposition principle. From this, it can be seen that the effective prestress probability superposition of the component with two rebars is shown in the formula (23), and the three-sub-distribution Gaussian mixture model is formed after the superposition of the two-sub-distribution model.

$$\Phi_2 = \qquad (23)$$
$$\omega_1^2 p(x \mid 2\mu_1, 2s_1^2) + 2\omega_1\omega_2 p(x \mid \mu_1 + \mu_2, s_1^2 + s_2^2) + \omega_2^2 p(x \mid 2\mu_2, 2s_2^2)$$

Similarly, when the component is provided with T rebars, T−1 times of superpositions are carried out corresponding to the Gaussian mixture model, as shown in a formula (24).

$$\Phi_T = \sum_{r=0}^{T} \omega_r p\left(x \mid (T-r)\mu_1 + r\mu_2, \sqrt{(T-r)s_1^2 + rs_2^2}\right) \quad (24)$$

wherein, $\omega_r$ is a weight coefficient, and is a single item corresponding to polynomial $(\omega_1+\omega_2)^T$ factorization polynomial, i.e. $\omega_r = C_r \omega_1^{T-r} \omega_2^r$, $C_r$ is a single item coefficient, $r=0, 1, 2, \ldots, T$, as shown in Table 1.

TABLE 1

| weight coefficient calculation | | | | | | |
|---|---|---|---|---|---|---|
| | r = 0 | r = 1 | r = 2 | r = 3 | r = 4 | ... r = T |
| Superposition of two rebars | $\omega_1^2$ | $2\omega_1\omega_2$ | $\omega_2^2$ | | | |
| Superposition of three rebars | $\omega_1^3$ | $3\omega_1^2\omega_2$ | $3\omega_1\omega_2^2$ | $\omega_2^3$ | | |
| Superposition of four rebars | $\omega_1^4$ | $4\omega_1^3\omega_2$ | $6\omega_1^2\omega_2^2$ | $4\omega_1\omega_2^3$ | $\omega_2^3$ | |
| ... | ... | ... | ... | ... | ... | ...... |
| Superposition of T rebars | $\omega_1^T$ | $C_1\omega_1^{T-1}\omega_2$ | $C_2\omega_1^{T-2}\omega_2^2$ | $C_3\omega_1^{T-3}\omega_2^3$ | $C_4\omega_1^{T-4}\omega_2^4$ | ... $\omega_2^T$ |

When the actually measured effective prestress of the structure is subjected to an N-sub-Gaussian mixture model (N=3, 4, 5), the effective prestress probability density of the component can be calculated by referring to the superposition principle of the two-sub-distribution Gaussian mixture model proposed by the present disclosure. The evaluation characteristic value $\hat{\sigma}_{pe}$ of the effective prestress of the component may be determined by means of integration

DESCRIPTION OF THE ACCOMPANYING DRAWINGS

In order to more clearly illustrate the embodiments of the present disclosure or the technical solutions in the prior art, the drawings that are required to be used in the embodiments or the description of the prior art will be briefly described below, and it is obvious that the drawings in the following description are only embodiments of the present disclosure, and that other drawings can be obtained according to the provided drawings without inventive effort for a person skilled in the art.

DETAILED DESCRIPTION OF THE EMBODIMENTS

The following description of the embodiments of the present disclosure will be made clearly and completely with reference to the accompanying drawings, in which it is apparent that the embodiments described are only some embodiments of the present disclosure, but not all embodiments. All other embodiments, which can be made by those skilled in the art based on the embodiments of the disclosure without making any inventive effort, are intended to be within the scope of the disclosure.

Figure 1:
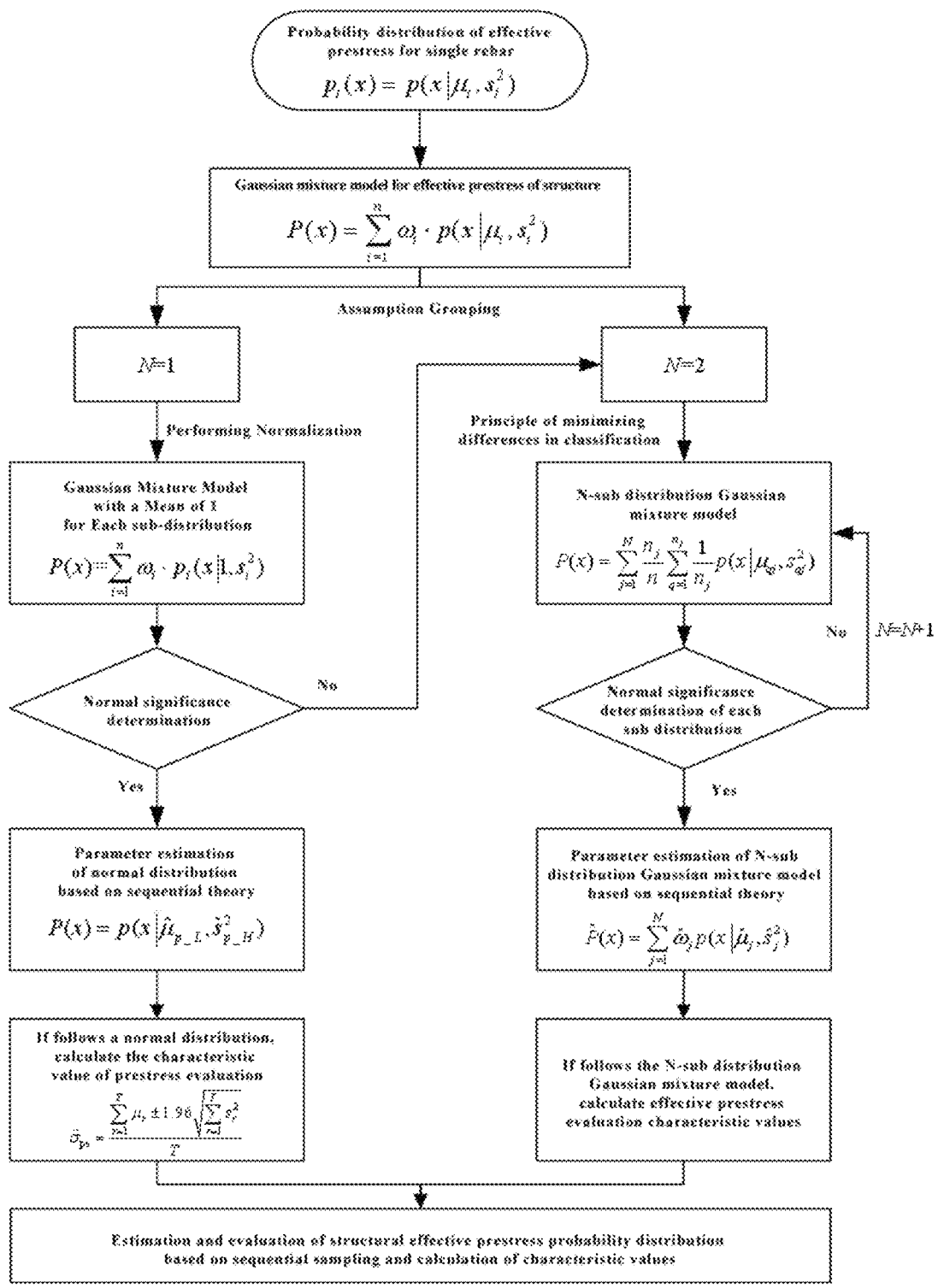
FIG. 1 is a flow chart of a method for estimating effective prestress and calculating evaluation characteristic value of the structure based on sequential sampling.

Referring to FIG. 1, the embodiment of the disclosure discloses a method for estimating effective prestress and calculating evaluation characteristic value of concrete structure, which specifically includes the following steps:

S1, calculating effective prestress probability distribution of a concrete structure prestress rebar;

S2, establishing a Gaussian mixture model of effective prestress of the concrete structure;

S3, carrying out normalization processing and normal significance judgment on the Gaussian mixture model;

S4, sampling and estimating the effective prestress probability distribution of the structure with normal distribution in theoretical distribution;

S5, calculating effective prestress evaluation characteristic values of components under the normal distribution condition;

S6, grouping processing and normal significance judging of the Gaussian mixture model;

S7, sampling and estimating the structural effective prestress probability distribution of the N-sub-distribution Gaussian mixture model by theoretical distribution;

S8, calculating effective prestress evaluation characteristic values of the components under the condition of the N-sub-distribution Gaussian mixture model.

EMBODIMENT

The beams and slabs of the engineering building all adopt the unbonded prestress technology, which are of unbonded prestress concrete wide flat beam frame shear wall structures, and have the building area of about 43 thousand square meters and 9 layers. The reinforcement and transformation are planned 19 years after construction is completed and the effective prestress level in the structure is to be evaluated. The prestress rebars of the engineering are 1570 MPa steel strands, the tensile control stress is 70% of the tensile strength of the prestress rebars, and the strength of the concrete beam is C35.

Considering the significant difference of the effective prestress design values of the beams and slabs in the structure, classification testing and evaluation of the effective prestress in beams and slabs are carried out.

Sampling evaluation of prestress rebars in beam

1. The design conditions of the prestress rebars in the beams and the number of the prestress rebars (n=1817) were obtained through a design drawing, wherein the maximum estimation error was required to be controlled within 5%.

1. Normalization Treatment and Normal Significance Verification of Theoretical Model.

Figure 2:
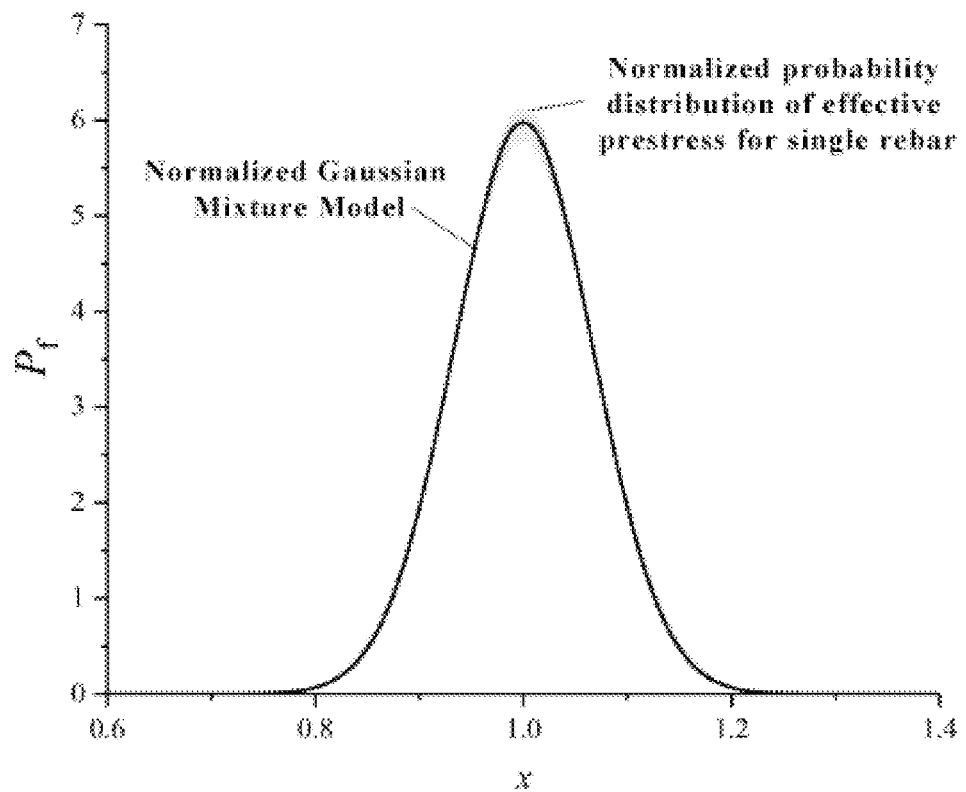
FIG. 2 is a diagram of a normalized Gaussian mixture model provided by an embodiment of the disclosure.

An effective prestress Gaussian mixture model of the structural beams was calculated according to the steps S1 and S2, normalization treatment was performed on effective prestress of prestress rebars in the beams to form a Gaussian mixture model with the mean value of each sub-distribution being 1, whose kurtosis was calculated to be K=3.08, and the difference between the two models was D(x)=0.023<0.05. From the results, the Gaussian mixture model can be verified in the step S3, which shows that it can be approximately sampled and evaluated by using a normal distribution, and the theoretical distribution is shown in FIG. 2 and formula (25).

$$P(x) = p(x \mid 1, 0.067^2) \qquad (25)$$

2. Extracting a First Batch of Samples of the Prestress Rebar

The number of samples extracted in the first batch is Item 3.3.10 according to the Technical Standard for Building Structure Detection (GB/T50344-2019), and 125 samples are extracted in combination with engineering types. The effective prestress of unbonded prestress rebars is directly measured on site by adopting a pull-off method, and the measured effective prestress value is divided by the design mean value of the prestress rebars to form normalized measured data $\tilde{X}_1 = (\tilde{x}_1, \tilde{x}_2, \ldots, \tilde{x}_{125})$ 3. Performing a Replacement Sampling on the First Batch of Samples that have been Extracted by the Bootstrap Method 100000 rounds of sampling with replacement were performed to generate the sample space required for characteristic value estimation $\{\tilde{X}_1\}$, the characteristic value of 95% guarantee rate of each Bootstrap sample $\hat{F}_{125}$ was calculated, a characteristic value probability density function $P(\hat{F})$ was then formed, and its 95% confidence interval length $l_{F125}$ was calculated.

Through KS verification, 95% assurance characteristic value can accept normal assumption, the mean value of the characteristic value $\hat{F}_{\mu 125}=0.91$, the Characteristic value variance $\hat{s}_{125}^2=0.000169$, the Confidence interval length $l_{F125}=3.92\times s_{125}=0.051$ the estimation error $\lambda=l_{F125}/\hat{F}_{\mu 125}=0.0559>0.05$, which does not meet the predetermined requirement.

4. the Sampling Sample is Supplemented, and the Estimation Error of the Characteristic Value is Calculated.

Figure 3:
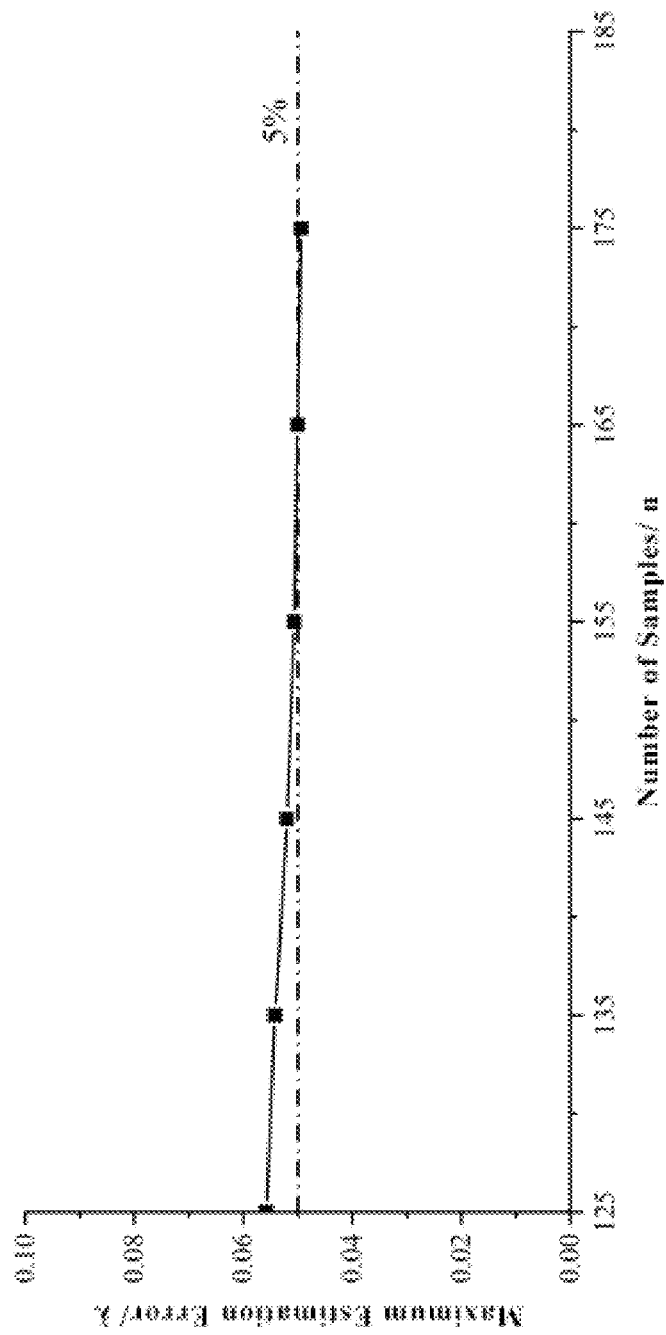
FIG. 3 is a graph showing a variation rule of the maximum estimation error of effective prestress of a beam with the number of samples according to the embodiment of the present disclosure.

The measured samples are supplemented to expand the sample information and improve the accuracy of estimation. 10 measured samples (m=10) were supplemented each time, and steps ((2) to (3)) in S4 are repeated, see FIG. 3. When the number of samples is increased to 175, the effective prestress force is 95% and the average value of the assurance characteristic values is obtained $\hat{F}_{\mu 175}=0.91$, $\hat{s}_{175}^2=0.000132$. The 95% confidence interval Length $l_{F175}=3.92*s_{175}=0.045$, the maximum estimation error $\lambda=l_{F175}/\hat{F}_{\mu 175}=0.049<0.05$, indicating that 175 samples can guarantee that characteristic value estimation error be controlled within 5%.

5. Establishing Measured Probability Estimation Model of Effective Prestress of Structure For the 175 samples $\tilde{X}_p$, the sampling is performed with replacement for 100000 rounds, and the average value of each sampling result is calculated $P(\mu_p)$ And the probability density function variance $P(\hat{s}_p)$, and the lower limit of the mean value and the upper limit of the variance were taken as characteristic parameters to estimate the actual probability distribution of the effective prestress of the structure.

$$\hat{P}(x) = p(x \mid 1.073, 0.12^2) \qquad (26)$$

For the probability distribution of the effective prestress of the single rebar, inverse normalization treatment can be carried out, the design mean value corresponding to the prestress rebar is multiplied, and the measured probability estimation model is as follows:

$$\hat{p}_i(x) = p(x \mid 1.073\mu_i, 0.12^2\mu_i^2) \qquad (27)$$

For example, the effective prestress design value of the ith rebar is 754 MPa, and the probability distribution of the prestress rebar is:

$$\hat{p}_j(x) = p(x \mid 809, 90.48^2) \qquad (28)$$

6. Evaluation Characteristic Value Calculation of Effective Prestress of Beam Structure taking a typical prestressed concrete beam as an example, the effective prestress evaluation characteristic value of the beam component $\hat{\sigma}_{Pe}$ was calculated. The beam is internally provided with 12 prestress rebars, the probability distribution of each rebar is calculated by the formula (27), and the probability distribution is respectively 6 $\hat{p}_i(x)=p(x|809,90.48^2)$ and 6 $\hat{p}_i(x)=p(x|751, 84.02^2)$. Based on the normal distribution superposition principle of the step S5, the evaluation characteristic values of the effective prestress of the beam component are as follows:

$$\hat{\sigma}_{pe} = \frac{\sum_{r=1}^{12}\mu_r - 1.96\sqrt{\sum_{r=1}^{12}s_r^2}}{12} = 730.6 \text{ MPa} \qquad (29)$$

2. Sampling Evaluation of Prestress Rebar in Slab

The design conditions of the prestress rebars in the slab and the number of the prestress rebars (n=3587) were obtained through a design drawing, wherein the maximum estimation error is required to be controlled within 5%.

1. Normalization Treatment and Normal Significance Verification of Theoretical Model an effective prestress Gaussian mixture model of the structural beam was calculated according to the steps S1 and S2. A normalization treatment on the effective prestress of the prestress rebar in the slab was performed to form the Gaussian mixture model with the mean value of each sub-distribution being 1, and calculating the kurtosis of the Gaussian mixture model to be K=3.69>3.5. From the results, the Gaussian mixture model does not pass the S3 step verification and the step S2 is required to be returned to arrange the mean and the variance of the Gaussian mixture model from large to small into 2 groups (N=2), see the formula (30) below $$P(x) = \sum_{i=1}^{n} \frac{1}{n} \cdot p(x \mid \mu_i, s_i^2) = \sum_{q=1}^{n_1} \frac{1}{n_1} p(x \mid \mu_{q1}, s_{q1}^2) + \sum_{q=1}^{n_2} \frac{1}{n_2} p(x \mid \mu_{q2}, s_{q2}^2) \quad (30)$$

Figure 4:
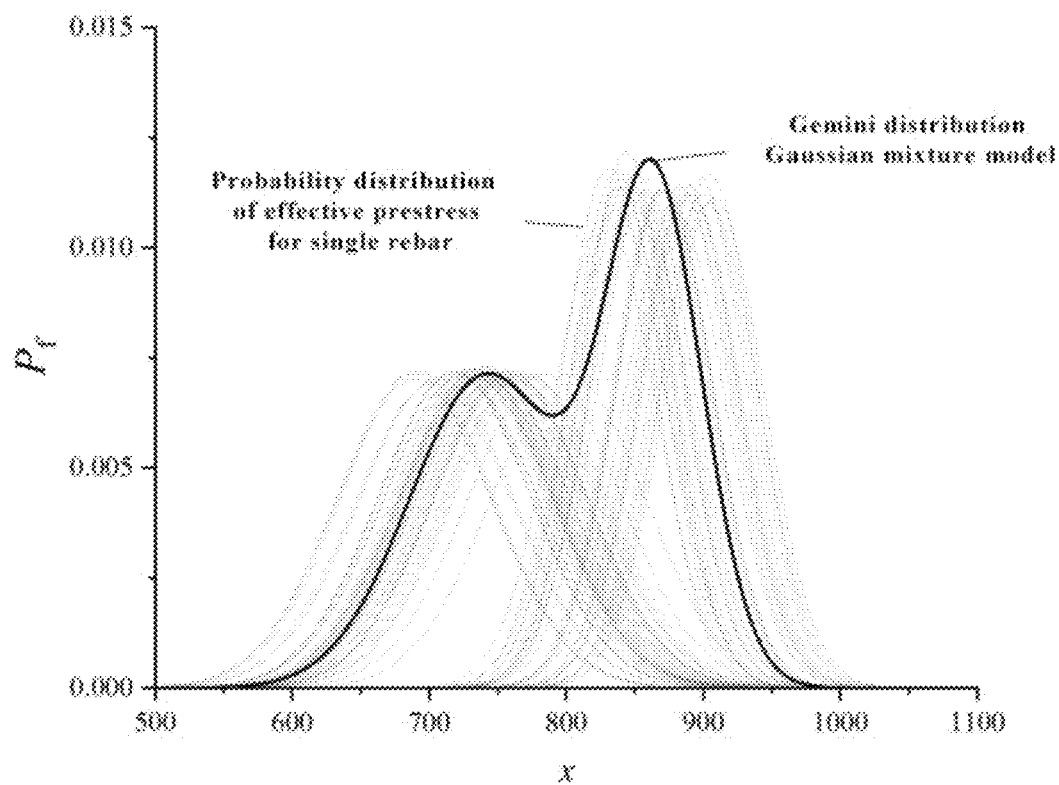
FIG. 4 is a diagram of a Gaussian mixture model with two sub-distributions according to an embodiment of the disclosure.

The normal significance of each group of Gaussian mixture models is verified through the S5 step. The calculated results are that the skewness s=0.07<0.2 and the kurtosis k=3.12<3.5 for group 1. The skewness s=0.09<0.2, kurtosis k=3.07<3.5 for the group 2. Both sets of gaussian mixture models can pass the normal significance verification, and the gaussian mixture model in the slab can be approximately converted into a binary distributed gaussian mixture model, see FIG. 4 and equation (31).

$$P(x) \approx \omega_1 p(x \mid \mu_1, s_1^2) + \omega_2 p(x \mid \mu_2, s_2^2) \approx$$
$$0.59 p(x \mid 742, 56.08^2) + 0.41 p(x \mid 864, 35.29^2)$$

2. Extracting a First Batch of Prestress Rebar Samples

The number of samples extracted in the first batch is based on the item 3.3.10 of the Technical Standard for Detecting Building Structure (GB/T50344-2019), and the sampling number is 200. The effective prestress of the unbonded prestress rebars is directly measured on site by adopting a pull-off method, and measured data are obtained $\tilde{X}_1 = (\tilde{x}_1, \tilde{x}_2, \ldots, \tilde{x}_{200})$ 3. Sampling the First Sampled Sample with Replacement by the Bootstrap Method 100000 rounds of sampling with replacement were performed to generate the sample space required for characteristic value estimation $\{\tilde{X}_1\}$. Parameter estimation is carried out on each sampling result by using an EM algorithm, and a 95% guarantee rate characteristic value of each sampling result is calculated according to the S6 method $\hat{F}_{200}$, forming characteristic value probability density function $P(\hat{F}_{200})$ under 200 sampling conditions and its 95% confidence interval length $l_{F200}$ was calculated.

Through the KS test, 95% assurance characteristic value can accept normal assumption, calculating characteristic value mean value $\hat{F}_{\mu 200}$=658.03 MPa Characteristic value variance $\hat{S}_{200}^2$=106.69 Feature value 95% confidence interval length $l_{F200}$=3.92×$s_{200}$=40.49, maximum estimation error $\lambda = l_{F200}/\hat{F}_{\mu 200}$=0.062>0.05 The predetermined requirement cannot be satisfied.

4. The Sampling Sample is Supplemented, and the Estimation Error of the Characteristic Value is Calculated.

Figure 5:
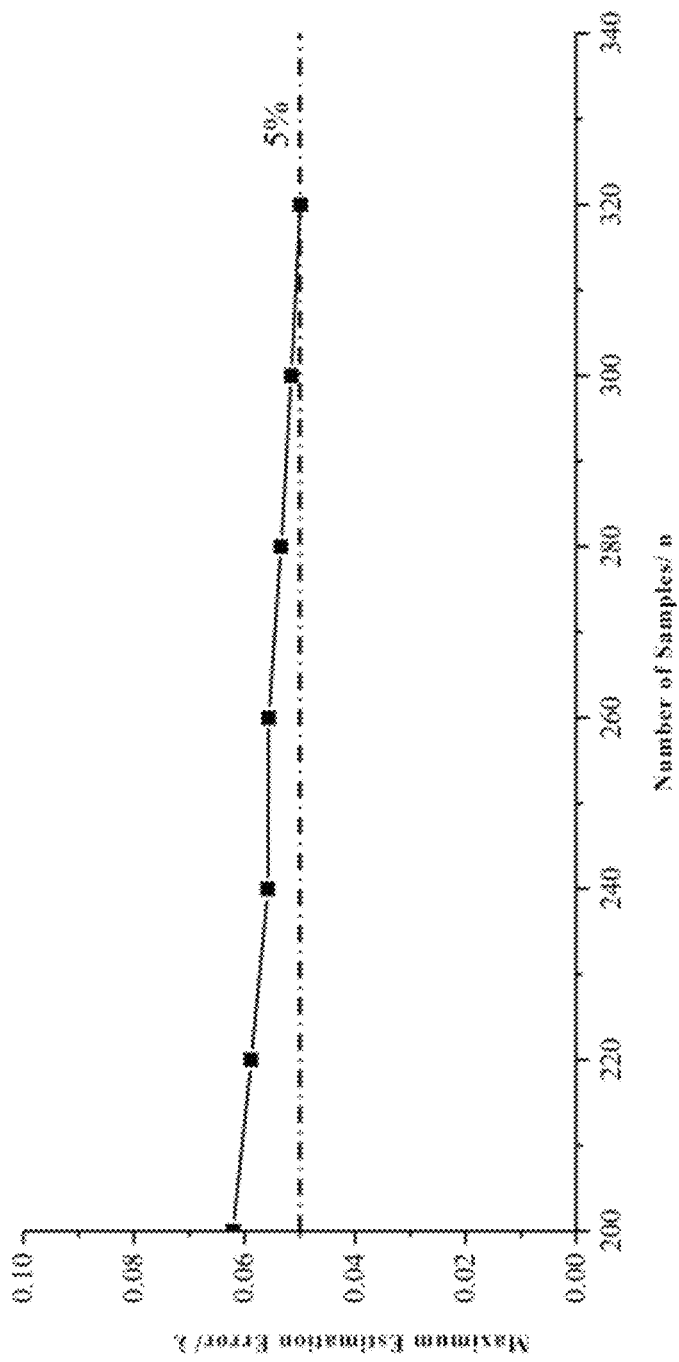
FIG. 5 is a graph showing a variation rule of the maximum estimation error of effective prestress of a slab with the number of samples according to the sample number.

The actual samples are supplemented to expand the sample information and provide the accuracy of the estimation, 20 samples (m=20) were supplemented each time, steps ((2) to (3)) in S7 are repeated, see FIG. 5, and when the number of samples is increased to 320, the mean value of the effective prestress 95% assurance characteristic values is calculated to be $\hat{F}_{\mu 320}$=650.91, $\hat{s}_{320}^2$=68.70. The Feature value 95% confidence interval length was calculated to be $l_{F320}$=3.92×$s_{320}$=32.49, and the maximum estimation error $\lambda = l_{F320}/\hat{F}_{\mu 320}$=0.049<0.05, indicating that the 320 samples can ensure that the characteristic value estimation error be controlled within 5%.

5. The Measured Probability Estimation Model of Effective Prestress of Structure is Formed.

Estimating each control parameter of the sample by the EM algorithm $\tilde{X}_{320}$, to obtain the weight $\hat{\omega}_j$, the Mean $\hat{\mu}_j$ and the variance $\hat{s}_j^2$. The substituting those values into the formula (20) to obtain the effective prestress probability distribution of the structure as shown in the following formula:

$$\hat{P}(x) = 0.61 p(x \mid 756.03, 72.1^2) + 0.39 p(x \mid 957.45, 35.29^2) \quad (32)$$

The effective prestress of the single rebar is also subject to the distribution:

$$\hat{p}(x) = 0.61 p(x \mid 756.03, 72.1^2) + 0.39 p(x \mid 957.45, 35.29^2) \quad (33)$$

6. Evaluation Characteristic Value Calculation of Effective Prestress of Slab Structure Taking a typical prestressed concrete slab as an example, calculation of the effective prestress evaluation characteristic values of slab structure $\hat{\sigma}_{pe}$ was performed. 124 prestress rebars are arranged in the slab, the probability distribution of each rebar is shown as (33), and the probability distribution of the effective prestress of the slab component is as follows based on the superposition principle of the binary distribution Gaussian mixture model in the step S8:

$$\Phi_T = \sum_{r=0}^{T} \omega_r p\left(x \mid (k-r)\mu_1 + r\mu_2, \sqrt{(T-r)s_1^2 + rs_2^2}\right) \quad (34)$$

The evaluation characteristic value of the effective prestress of the slab component can be calculated by integrating the formula (34), and the value of x is calculated when the area is 95%, wherein x is the evaluation characteristic value of the effective prestress.

$$\hat{\sigma}_{pe} = 834.58 \text{ MPa} \quad (35)$$

In the specification, each embodiment is described in a progressive manner, and each embodiment is mainly described in a different point from other embodiments, and identical and similar parts between the embodiments are all enough to refer to each other. For the device disclosed in the embodiment, since it corresponds to the method disclosed in the embodiment, the description is relatively simple, and the relevant points refer to the description of the method section.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

What is claimed is:

1. A method for estimating effective prestress and calculating evaluation characteristic value of a concrete structure, comprising the following steps:
   S1, calculating effective prestress probability distribution of prestress rebars of the concrete structure;
   S2, establishing a Gaussian mixture model of effective prestress of the concrete structure;

S3, carrying out normalization processing and normal significance judgment on the Gaussian mixture model;

S4, actually sampling and estimating the effective prestress probability distribution of the concrete structure with normal distribution in theoretical distribution;

S5, calculating effective prestress evaluation characteristic values of components under the normal distribution condition;

S6, grouping processing and normal significance judging of the Gaussian mixture model;

S7, sampling and estimating the structural effective prestress probability distribution of the N-sub-distribution Gaussian mixture model by theoretical distribution;

S8, calculating effective prestress evaluation characteristic values of the components under the condition of the N-sub-distribution Gaussian mixture model; and S9, performing reinforcement and transformation based on the effective prestress evaluation characteristic values;

wherein in step S8: when an actually measured distribution of the effective prestress of the concrete structure approximately is subjected to an N-sub-distribution Gaussian mixture model, N=2, 3 and 4, . . . , the effective prestress of a single rebar also obeys the N-sub-distribution Gaussian mixture model;

when the actually measured effective prestress of the concrete structure is a two-sub-distribution Gaussian mixture model, namely N=2, a formula (22) is shown;

$$\hat{p}(x) = \hat{\omega}_1 p(x|\hat{\mu}_1, \hat{s}_1^2) + \hat{\omega}_2 p(x|\hat{\mu}_2, \hat{s}_2^2) \tag{22}$$

wherein, x is the effective prestress, $\hat{\omega}_j$ is the weight, $\hat{\mu}_j$ is the mean of the j-th sub distribution of the Gaussian mixture model, and $\hat{s}_j$ is the variance of the j-th sub distribution of the Gaussian mixture model;

when two rebars exist in the component, the Gaussian mixture model superposition can be regarded as mutual superposition between two normal sub-distributions with weights, a probability of simultaneous occurrence and mutual superposition of a sub-distribution $p(x|\hat{\mu}_1, \hat{s}_1^2)$ and a sub-distribution $p(x|\hat{\mu}_2, \hat{s}_2^2)$ is $2\omega_1\omega_2$; because each sub-distribution is normal distribution, the average value and the variance after superposition can be calculated through the normal distribution superposition principle, the effective prestress probability superposition of the component with two rebars is shown in the formula (23), and the three-sub-distribution Gaussian mixture model is formed after the superposition of the two-sub-distribution model. the effective prestress probability superposition of the component with two rebars is shown in a formula (23), and a three-sub-distribution Gaussian mixture model is formed after the superposition of the two-sub-distribution models;

$$\Phi_2 = \tag{23}$$
$$\omega_1^2 p(x|2\mu_1, 2s_1^2) + 2\omega_1\omega_2 p(x|\mu_1+\mu_2, s_1^2+s_2^2) + \omega_2^2 p(x|2\mu_2, 2s_2^2)$$

similarly, when the component is provided with Trebars, T−1 times of superpositions are carried out corresponding to the Gaussian mixture model, as shown in a formula (24);

$$\Phi_T = \sum_{r=0}^{T} \omega_r p\left(x \mid (T-r)\mu_1 + r\mu_2, \sqrt{(T-r)s_1^2 + rs_2^2}\right) \tag{24}$$

wherein, $\omega_r$ is a weight coefficient, and is a single item corresponding to polynomial $(\omega_1+\omega_2)^T$ factorization polynomial, i.e $\omega_r = C_r \omega_1^{T-r} \omega_2^r$, $C^r$ is a single item coefficient, r=0, 1,2, . . . , T;

when the actually measured effective prestress of the concrete structure is subjected to an N-sub-Gaussian mixture model (N=3, 4, 5), the effective prestress probability density of the component is calculated based on the superposition principle of the two-sub-distribution Gaussian mixture model, and the evaluation characteristic value of the effective prestress of the component is determined by means of integration.

2. The method of claim 1, wherein in the S1, the method comprises the steps of counting the number n of the prestress rebars in the concrete structure; calculating effective prestress probability distribution (i=1, 2, . . . n) of an i-th prestress rebar in the prestress concrete structure by Monte Carlo method; and establishing a normal distribution probability density curve, shown as a formula (1):

$$p_i(x) = p_i(x|\mu_i, s_i^2) = \frac{1}{\sqrt{2\pi}\, s_i} \exp\left(-\frac{(x-\mu_i)^2}{2s_i^2}\right) \tag{1}$$

wherein x is the effective prestress, $\mu_i$ is a design value of effective prestress for the i-th rebar, namely the mean value of the probability distribution, s, is the standard deviation.

3. The method of claim 2, wherein in the S2, the method comprises the steps of taking a set of effective prestress probability distribution of all the prestress rebars in a structure prestress system as a whole, and defining the set as the effective prestress probability distribution of the concrete structure; obtaining the probability density $p_i(x)$ of the effective prestress of the i-th (i=1, 2, . . . , n) single rebar of the concrete structure through the step S1, and carrying out probability density superposition on the same to form a Gaussian mixture model of the effective prestress of the concrete structure, as shown in a formula (2)

$$P(x) = \sum_{i=1}^{n} \frac{1}{n} \cdot p_i(x|\mu_i, s_i^2) = \sum_{i=1}^{n} \frac{1}{n} \cdot \frac{1}{\sqrt{2\pi}\, s_i} \exp\left(-\frac{(x-\mu_i)^2}{2s_i^2}\right). \tag{2}$$

4. The method of claim 3, wherein in step S3: the method comprises the steps of dividing random variables of the effective prestress of all the single rebars by the corresponding design value $\mu_i$ to form a normalized structure effective prestress Gaussian mixture model, wherein the normalized structure effective prestress Gaussian mixture model is shown as a formula (3);

$$P(x) = \sum_{i=1}^{n} \frac{1}{n} \cdot \frac{1}{\sqrt{2\pi}\,(s_i/\mu_i)} \exp\left(-\frac{(x-1)^2}{2(s_i/\mu_i)^2}\right) \tag{3}$$

wherein a skewness of the Gaussian mixture model with the same mean of sub distributions is S=0, and the kurtosis K is calculated by adopting the formula (4):

$$K = \frac{\sum_{i=1}^{n} \omega_i \cdot 3(s_i/\mu_i)^4}{\left(\sum_{i=1}^{n} \omega_i \cdot (s_i/\mu_i)^2\right)^2} \quad (4)$$

if the kurtosis is located in the [3,3.5] interval, the distribution is preliminarily considered to be approximately compliant with normal distribution;

mean $\mu=1$ and variance $$s^2 = \frac{1}{n}\sum_{i=1}^{n}(s_i/\mu_i)^2 \quad $$

based on equation (3), establishing a normal distribution model as shown in a formula (5):

$$N(x) = \frac{1}{\sqrt{2\pi}s}\exp\left(-\frac{(x-1)^2}{2s^2}\right) \quad (5)$$

and establishing a difference function $D(x)=P(x)-N(x)$ of the Gaussian mixture model and the normal distribution model, wherein the monotonicity shows that $D(x)$ is the maximum value at the position of $x=1$, and only the difference value is required to be judged to be within 5%, as shown in a formula (6), and the normal distribution approximation representation can be adopted for determining the Gaussian mixture model;

$$\frac{P(1)-N(1)}{N(1)} \leq 5\%. \quad (6)$$

5. The method of claim 1, wherein in step S4: based on the concept of sequential sampling, measured sampling estimation is carried out on the effective prestress of the concrete structure:

① considering that the effective prestress of the concrete structure obeys the normal overall, as shown in a formula (7); wherein $\mu$ and $S^2$ are both unknown; randomly sampling and detecting effective prestress of a prestress rebar in the concrete structure to obtain real-time effective prestress of the prestress rebar, and dividing the real-time effective prestress by a design value of the prestress rebar; the first batch of sampling totally extracts k rebars to form an initial sample $\tilde{X}_1=(\tilde{x}_1,\tilde{x}_2,\ldots,\tilde{x}_k)$;

$$P(x) = p(x\,|\,\mu, s^2) \quad (7)$$

② adopting the Bootstrap method, performing sampling with replacement on sample $\tilde{X}_1$ k×B times to form B Bootstrap samples capable of reflecting overall statistical characteristics, as shown in a formula (8), wherein a column of the matrix is a Bootstrap sample, and B is taken 100000 times at least; calculating the characteristic value $\hat{F}$ of 95% guarantee rate of each Bootstrap sample to form a characteristic value probability density function $P(\hat{F})$, and calculating 95% confidence interval length $l_F$;

$$\{\tilde{X}_1\} = (\tilde{x}_1,\tilde{x}_2,\ldots,\tilde{x}_k) = \begin{bmatrix} \tilde{x}_{11} & \tilde{x}_{12} & \ldots & \tilde{x}_{1B} \\ \tilde{x}_{21} & \tilde{x}_{22} & \ldots & \tilde{x}_{2B} \\ \vdots & \vdots & \ddots & \vdots \\ \tilde{x}_{k1} & \tilde{x}_{k2} & \ldots & \tilde{x}_{kB} \end{bmatrix} \quad (8)$$

③ if the maximum error is $\lambda=l_F/\hat{F}^\mu \leq 0.05(0.1)$, then considering the estimation accuracy of the sample $\tilde{X}_1$ meets the predetermined requirement, wherein $\hat{F}_\mu$ is the average value of $P(\hat{F})$; if $\lambda=l_F/\hat{F}_\mu>0.05(0.1)$, then considering the estimation of the sample $\tilde{X}_1$ on the characteristic value cannot meet the preset requirement, extracting m samples continuously to supplement the total sample number to k+m and form the actually measured sample $\tilde{X}_2=(\tilde{x}_1,\tilde{x}_2,\ldots,\tilde{x}_{k+m})$;

④ using $\tilde{X}_2$ as a sample and repeating the steps ② to ③, when the estimation accuracy requirement is not met, adding m samples each time, repeating p−1 times in total until the estimation accuracy requirement is met, namely, maximum estimation error $\lambda=l_F/\hat{F}_\mu \leq 0.05(0.1)$, and finally forming sample $\tilde{X}_p=(\tilde{x}_1,\tilde{x}_2,\ldots,\tilde{x}_{k+(p-1)m})$;

⑤ performing sample expansion processing on $\tilde{X}_p$ by Bootstrap method to form probability density function $P(\hat{\mu}_p)$ and $P(\hat{s}_p)$ of mean and variance; calculating 95% confidence interval of the two parameters $[\hat{\mu}_{p\_L}, \hat{\mu}_{p\_H}]$ and $[\hat{s}_{p\_L}^2, \hat{s}_{p\_H}^2]$ respectively; to ensure the safety of the concrete structure, using the lower limit $\hat{\mu}_{p\_L}$ of the mean and the upper limit $\hat{s}_{p\_H}^2$ of the variance as characteristic parameters, substituting the characteristic parameters into the formula (7) to obtain an measured probability estimation model of the effective prestress of the concrete structure, as shown in a formula (9);

$$\hat{P}(x) = p(x\,|\,\hat{\mu}_{p\_L}, \hat{s}_{p\_H}^2) \quad (9)$$

⑥ performing inverse normalization treatment on the formula (9), and multiplying the design value $\mu_i$ of each prestress rebar of the concrete structure to calculate an measured probability estimation model of each effective prestress of the single rebar, as shown in a formula (10)

$$\hat{p}_i(x) = p(x\,|\,\mu_i\hat{\mu}_{p\_L}, \mu_i^2\hat{s}_{p\_H}^2). \quad (10)$$

6. The method of claim 5, wherein in step S5:
when the effective prestress of the actually measured structure is subjected to normal distribution, the effective prestress of the single rebar is subjected to normal distribution as well as the formula (10), and the effective prestress probability distribution of the component is the superposition of a plurality of normal distributions; based on the normal distribution superposition principle, the effective prestress probability distribution of the component with T prestress rebars is expressed as follows:

$$\Phi_T = p\left(x\,\bigg|\,\sum_{R=1}^{T}\mu_R, \sum_{R=1}^{T}s_R^2\right) \quad (11)$$

wherein $\mu_R$ and $s_R$ are the measured estimated mean and standard deviation of the effective prestress of each single rebar in the component respectively obtained by the formula (10), wherein R is the number of the prestress rebar in the component, R=1, 2, . . . , T;

the upper/lower limit of the 95% confidence interval is adopted as the characteristic value for evaluating the effective prestress distribution in the component $\hat{\sigma}_{pe}$, as shown in a formula (12); when the component is favorable, the lower limit of the 95% confidence interval is adopted for estimation, and the formula takes the negative sign;

when the component is unfavorable, the upper limit of the 95% confidence interval is adopted for estimation, and the formula takes the positive sign $$\hat{\sigma}_{pe} = \frac{\sum_{r=1}^{T} \mu_r \pm 1.96 \sqrt{\sum_{r=1}^{T} s_r^2}}{T}. \tag{12}$$

7. The method of claim 6, wherein in step S6: the method comprises the steps of returning to the step S2 when the above mentioned normal significance cannot be satisfied, arranging the effective prestress means and variances of all the single rebars in the formula (2) according to the sizes, and dividing the effective prestress means and variances into N groups so as to minimize the difference between the mean and the variances of each group, wherein the number of the prestress rebars in each group is nj; the Gaussian mixture model of the effective prestress of the concrete structure is shown as a formula (13);

$$P(x) = \sum_{i=1}^{n} \frac{1}{n} \cdot p(x \mid \mu_i, s_i^2) = \sum_{j=1}^{N} \frac{n_j}{n} \sum_{q=1}^{n_j} \frac{1}{n_j} p(x \mid \mu_{qj}, s_{qj}^2) \tag{13}$$

wherein j represents a grouping number, j=1, 2, . . . , N, $n_j$ represents the number of prestress rebars in each group, q represents the rebar number in the j-th group, q=1, 2, . . . , $n_j$), $\mu_{qj}$ and $s_{qj}^2$ are designing values and variances of the q-th rebar in the j-th group respectively;

kurtosis and skewness of each group of Gaussian mixture models are checked by the following formulas:

$$S = \frac{E[(x-\mu_j)^3]}{E[(x-\mu_j)^2]^{3/2}} \tag{14}$$

$$K = \frac{E[(x-\mu_j)^4]}{E[(x-\mu_j)^2]^2} \tag{15}$$

$$E[(x-\mu_j)^2] = \sum_{q=1}^{n_j} \frac{1}{n_j} s_{qj}^2 + \left[\sum_{q=1}^{n_j} \frac{1}{n_j} \mu_{qj}^2 - \mu_j^2\right] \tag{16}$$

$$E[(x-\mu_j)^3] = \tag{17}$$

$$3\left[\sum_{q=1}^{n_j} \frac{1}{n_j}(\mu_{qj} - \mu_j)\right] s_{qj}^2 + \sum_{q=1}^{n_j} \frac{1}{n_j} [\mu_q^3 - 3\mu_j \mu_{qj}^2 + 3\mu_j^2 \mu_{qj}] - 3\mu_j^3$$

$$E[(x-\mu_j)^4] = \sum_{q=1}^{n_j} \frac{1}{n_j} \cdot 3 s_{qj}^4 + \sum_{q=1}^{n_j} \frac{1}{n_j} \cdot (6\mu_{qj}^2 + 6\mu_j^2 - 12\mu_j \mu_{qj}) s_{qj}^2 + \tag{18}$$

$$\sum_{q=1}^{n_j} \frac{1}{n_j} \cdot (\mu_{qj}^4 - 4\mu_j \mu_{qj}^3 + 6\mu_j^2 \mu_{qj}^2, -4\mu_j^3 \mu_{qj}) + \mu_j^4$$

wherein: S is skewness, K is kurtosis, $E[(x-\mu_j)^2]$, $E[(x-\mu_j)^3]$ and $E[(x-\mu_j)^4]$ are the center distances of the second order, the third order and the fourth order of the j-th group respectively, $\mu_j$ is the mean of the design values for the j-th set of models, $$\mu_j = \sum_{q=1}^{n_j} \frac{1}{n_j} \mu_{qj};$$

if the skewness S of the j-th Gaussian mixture model is located in the [−0.2,0.2] interval and the kurtosis K is located in the [3,3.5] interval, the model can approximately obey normal distribution;

if the above N groups of Gaussian mixture models can pass the above normal significance test, the structural effective prestress Gaussian mixture model can be approximately converted into an N-sub-distribution Gaussian mixture model, so that each sub-distribution can be approximately represented by normal distribution, as shown in a formula (19);

$$P(x) = \sum_{i=1}^{n} \omega_i \cdot p(x \mid \mu_i, s_i^2) \approx \sum_{j=1}^{N} \omega_j p(x \mid \mu_j, s_j^2) \tag{19}$$

wherein, N is the number of groups, in actual engineering, N is firstly 2, if the normal significance criterion cannot be met, grouping is added, N=N+1 is enabled, and finally N sub-distributions can pass normal significance test; for general engineering, N is more than or equal to 2 and less than or equal to 5, $\omega_j$ is the weight of the j-th group.

8. The method of claim 7, wherein in step S7:

when the effective prestress probability distribution of the concrete structure can be processed and checked in the step S6, the effective prestress probability distribution of the concrete structure is considered to be from an approximate N-sub-distribution Gaussian mixture ensemble, as shown in a formula (20);

measured sampling estimation is performed on the effective prestress of the concrete structure by referring to the measured sampling estimation of normal distribution; the method comprises the following specific steps:

$$P(x) = \sum_{j=1}^{N} \omega_j p(x \mid \mu_j, s_j^2) \tag{20}$$

① considering that the effective prestress of the concrete structure obeys the N-sub-distribution Gaussian mixture mode, wherein $\omega_j$, $\mu_j$ and $S^2$ are unknown; taking a first sample from the population and extracting k initial samples $\tilde{X}_1 = (\tilde{x}_1, \tilde{x}_2, \ldots, \tilde{x}_k)$ ② adopting the Bootstrap method, performing sampling with replacement on sample $\tilde{X}_1$ k×B times to form B Bootstrap samples capable of reflecting overall statistical characteristics;

③ estimating the statistical parameters such as $\omega_j$, $\mu_j$ and $s_j$ for each Bootstrap sample by EM algorithm, obtaining the probability distribution $P(\hat{F})$ of the characteristic value with a 95% guarantee rate, and calculating 95% confidence interval length $l_F$;

④ if the maximum error is $\lambda = l_F/\hat{F}_\mu \leq 0.05(0.1)$, then considering the estimation accuracy of the sample $\tilde{X}_1$ meets the predetermined requirement; if $\lambda = l_F/\hat{F}_\mu > 0.05(0.1)$, then considering the estimation of the sample $\tilde{X}_1$ on the characteristic value cannot meet the preset requirement, extracting m samples continuously to supplement the total sample number to k+m and obtaining the actually measured sample $\tilde{X}_2 = (\tilde{x}_1, \tilde{x}_2, \ldots, \tilde{x}_{k+m})$;

⑤ using $\tilde{X}_2$ as a sample and repeating the steps ② to ③, when the estimation accuracy requirement is not met, adding m samples each time, repeating p−1 times in total until the estimation accuracy requirement, namely, maximum estimation error $\lambda = l_F/\tilde{F}_\mu \leq 0.05(0.1)$, is met, and finally forming sample $\tilde{X}_p = (\tilde{x}_1, \tilde{x}_2, \ldots, \tilde{x}_{k+(p-1)m})$;

⑥ estimating each control parameter of the sample $\tilde{X}_p$ by EM algorithm to obtain a weight $\hat{\omega}_j$, mean $\hat{\mu}_j$ and variance $\hat{s}_j$, substitute them into the formula (20) to obtain the effective prestress probability distribution of the concrete structure;

$$\hat{P}(x) = \sum_{j=1}^{N} \hat{\omega}_j p(x \mid \hat{\mu}_j, \hat{s}_j^2). \tag{21}$$

* * * * *